US008235898B2

(12) United States Patent
Bae et al.

(10) Patent No.: US 8,235,898 B2
(45) Date of Patent: Aug. 7, 2012

(54) ULTRASONIC DIRECT STRAIN ESTIMATION USING TEMPORAL AND SPATIAL CORRELATION

(75) Inventors: Unmin Bae, Seattle, WA (US); Yongmin Kim, Lake Forest Park, WA (US)

(73) Assignee: University of Washington through its Center for Commercialization, Seattle, WA (US)

( * ) Notice: Subject to any disclaimer, the term of this patent is extended or adjusted under 35 U.S.C. 154(b) by 1022 days.

(21) Appl. No.: 11/574,394

(22) PCT Filed: Aug. 29, 2005

(86) PCT No.: PCT/US2005/030674
§ 371 (c)(1),
(2), (4) Date: Sep. 12, 2007

(87) PCT Pub. No.: WO2006/026552
PCT Pub. Date: Mar. 9, 2006

(65) Prior Publication Data
US 2008/0287792 A1  Nov. 20, 2008

Related U.S. Application Data

(60) Provisional application No. 60/604,886, filed on Aug. 27, 2004.

(51) Int. Cl.
*A61B 8/00* (2006.01)
(52) U.S. Cl. ........ 600/437; 600/438; 600/440; 600/442; 600/443; 600/449; 600/587
(58) Field of Classification Search .................. 600/437, 600/440, 443, 447, 449, 589; 73/602, 573, 73/787
See application file for complete search history.

(56) References Cited

U.S. PATENT DOCUMENTS

| 5,424,743 | A | * | 6/1995 | Ghiglia et al. | 342/25 C |
|---|---|---|---|---|---|
| 5,524,636 | A | * | 6/1996 | Sarvazyan et al. | 600/587 |
| 5,816,923 | A | * | 10/1998 | Milo et al. | 464/58 |
| 6,029,487 | A | * | 2/2000 | Genin et al. | 72/58 |
| 2008/0287792 | A1 | * | 11/2008 | Bae et al. | 600/438 |
| 2010/0094131 | A1 | * | 4/2010 | Bae et al. | 600/438 |

OTHER PUBLICATIONS

O'Donnell, M., et al., "Internal Displacement and Strain Imaging Using Ultrasonic Speckle Tracking," IEEE Transactions on Ultrasonics, Ferroelectrics, and Frequency Control 41(3):314-325, May 1994.
Rabben, S.I., et al., "Ultrasound-Based Vessel Wall Tracking: An Auto-Correlation Technique With RF Center Frequency Estimation," Ultrasound in Medicine and Biology 28(4):507-517, Apr. 2002.

* cited by examiner

*Primary Examiner* — Tse Chen
*Assistant Examiner* — Baisakhi Roy
(74) *Attorney, Agent, or Firm* — University of Washington Center for Commercialization

(57) ABSTRACT

Strain is directly estimated in ultrasound elasticity imaging without computing displacement or resorting to spectral analysis. Conventional ultrasound elasticity imaging relies on calculating displacement and strain is computed from a derivative of the displacement. However, for typical parameter values used in ultrasound elasticity imaging, the displacement can be as large as a hundred times or displacement differences. If a tiny error in the calculation of displacement occurs, this could drastically affect the calculation of strain. By directly estimating strain, image quality is enhanced and the reduction in computational effort facilitates commercialization to aid in diagnosing disease or cancerous conditions.

18 Claims, 11 Drawing Sheets

ULTRASONIC DIRECT STRAIN ESTIMATION USING TEMPORAL AND SPATIAL CORRELATION

CROSS-REFERENCE TO RELATED APPLICATION

This application claims the benefit of U.S. Provisional Application No. 60/604,886, filed Aug. 27, 2004, which is incorporated herein by reference.

TECHNICAL FIELD

The present invention generally relates to measuring strain in biological structures.

BACKGROUND

Medical examination of the human body by touch, called palpation, reveals external abnormalities that may instigate additional investigation. In breast exams or prostate exams, clinicians use palpation to detect abnormal stiffness, which may point to diseased or cancerous bodily structures. Scientists have measured changes in the stiffness of biological structures by measuring their elasticity moduli ex vivo. For example, scientists have found that infiltrating ductile carcinomas are much stiffer than any other breast tissues, and prostate cancers are stiffer than normal prostate tissues. Stiff tissue has a high elasticity modulus and shows less strain under applied force than soft tissue. Thus, by applying compression and estimating the strain, stiffness in bodily structures can be obtained.

An early medical application of ultrasound imaging included the monitoring of blood flow by the use of the displacement technique. Strain can be computed from a derivative of the displacement. With this understanding, conventional elasticity imaging is based on estimating displacements from echoed ultrasound signals to calculate strain in bodily structures. However, conventional elasticity imaging suffers from both image quality and computational burden, which have prevented successful commercialization of the technology for clinicians to use. Because of the domination of the displacement technique, many attempts at improving the calculation of strain have focused on measuring displacement ever more accurately.

In medical ultrasound, strain in an object can be estimated using ultrasound echo signals acquired before and after object compression. Strain represents the amount of deformation and is defined as:

$$\frac{\Delta L}{L} \qquad (1)$$

where L is the length of an object and $\Delta L$ is the amount of change in the object length under uni-axial force. Conventional ultrasonic strain estimation methods are based on estimating displacements between ultrasound signals acquired before and after compression. Once displacements are estimated, strain is computed from a spatial derivative of the displacement as follows:

$$\frac{d_2 - d_1}{L} \qquad (2)$$

where $d_1$ and $d_2$ are the displacements at two different locations and L is the distance between these two locations (defined as the strain sample length).

For conventional strain estimation, displacements can be very large (e.g., more than a hundred micrometer), whereas the displacement difference converted to strain is very small (e.g., few micrometers). Consequently, if the strain were computed from large displacements, a tiny error in displacement estimation could magnify the error in the computation of the strain. Because strain constitutes such a small part of the displacement, scientists have resorted to displacement interpolation techniques to find the strain. To obtain desired results, hundreds of points may need to be interpolated, resulting in onerous computational effort, hindering production of marketable machinery.

SUMMARY

In accordance with this invention, a computer-readable medium, system, and method for calculating strain is provided. The method form of the invention includes a computer-implemented method for calculating strain that comprises transmitting and acquiring ultrasound signals echoed from an object before the object is compressed and after the object is compressed. The method further comprises estimating an amount of deformation of the object by using the phase of temporal and spatial correlation between ultrasound baseband signals from different frames so as to determine strain without having to estimate displacement.

In accordance with further aspects of this invention, a system form of the invention includes a system for calculating strain that comprises a temporal correlator for correlating groups of pixels of interest between two frames of baseband signals containing deformation information of an object. The system further comprises a spatial correlator for correlating information produced by the temporal correlator to render a complex number that contains information pertaining to an angular strain. The system yet further comprises a phase computer that calculates the phase of the complex number to obtain the angular strain. The system also comprises a gross motion vector estimator that locates correlated baseband signals from different frames and the results are provided to the temporal correlator. The system additionally comprises an angular strain converter, which takes the angular strain and converts it to strain.

In accordance with further aspects of this invention, a computer-readable medium form of the invention includes a storable computer-readable medium having computer-executable instructions thereon for implementing a method for calculating strain, which comprises transmitting and acquiring ultrasound signals echoed from an object before the object is compressed and after the object is compressed. The computer-readable medium also comprises estimating an amount of deformation of the object by using the phase of temporal and spatial correlation between ultrasound baseband signals from different frames so as to determine strain without having to estimate displacement.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
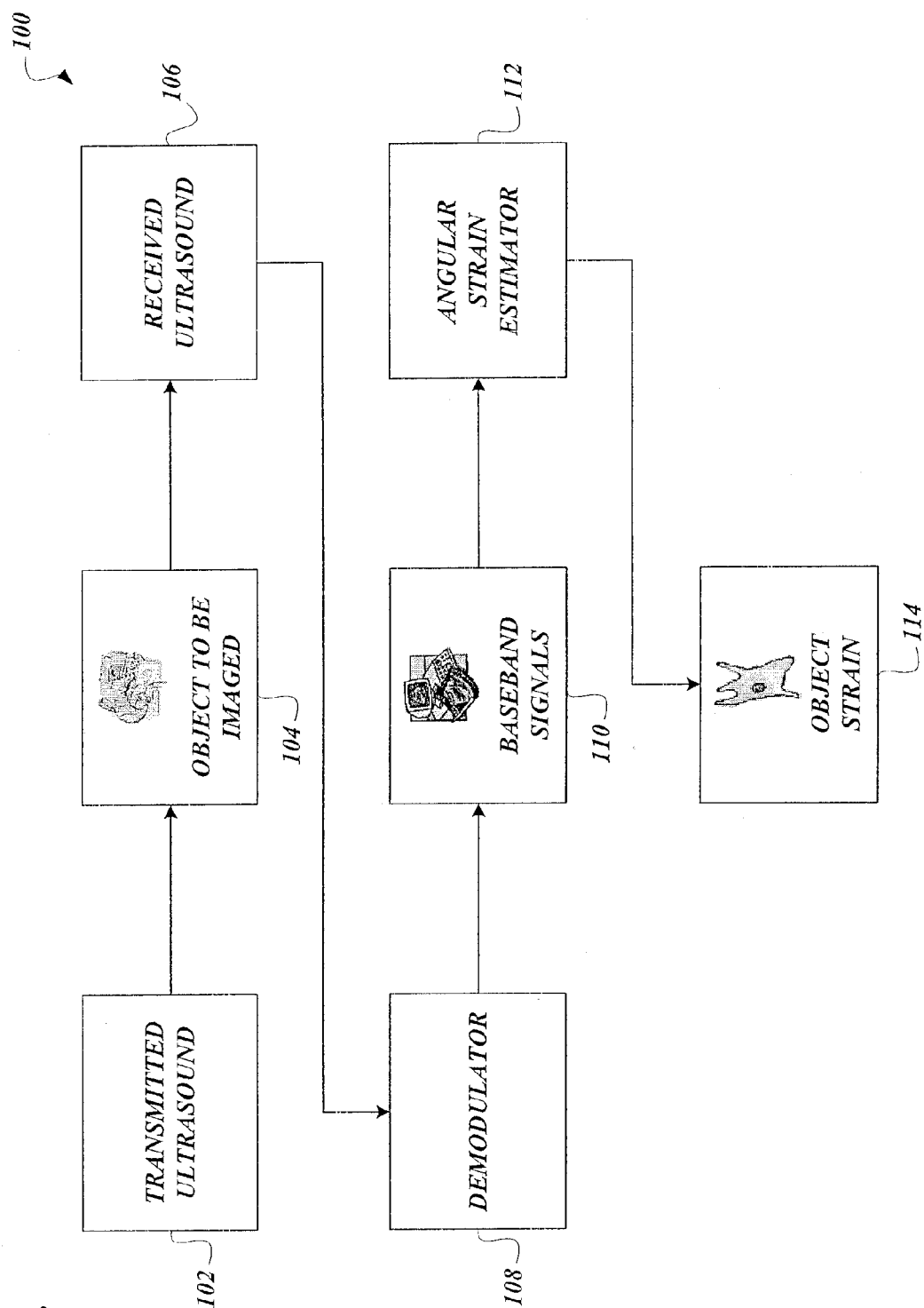
FIG. 1 is a block diagram illustrating an exemplary system for directly calculating strain using echoed ultrasound signals from bodily structures.

FIG. 1 illustrates a system 100 that directly calculates strain using baseband signals without the use of displacement. Transmitted ultrasound 102 is produced when an ultrasound transducer transmits pulses into an object 104 to be imaged. Received ultrasound 106 represents the ultrasound signals that are reflected back from boundaries of the object and/or scattered by scatterers in the object 104 to be imaged. The object 104 is compressed or expanded and its deformation is estimated by the system 100 using the received ultrasound 106. The compression or expansion source of force can be external, such as by a mechanical device (e.g., a vibrator) or by hand; or the compression or expansion source of force can be internal, such as by naturally occurring arterial pulsation.

The received ultrasound 106 is converted into radio-frequency electrical signals by the transducer that originally produced the transmitted ultrasound 102. The radio-frequency electrical signals have a carrier frequency, which is removed by a demodulator 108, resulting in complex baseband signals 110. As will be appreciated by one skilled in the art, any suitable ultrasound signals can be used in various embodiments of the present invention to calculate strain without the use of displacement. Although the following discussion uses the baseband signals 110 for calculation of strain, various embodiments of the present invention are not limited to the use of baseband signals, and other signals, such as radio-frequency signals, can be used for strain estimation.

The baseband signals 110 are provided to an angular strain estimator 112 which calculates the angular strain connected with the object prior to compression and after compression. Preferably, at least two pieces of ultrasound baseband data acquired at different times are used in estimating the angular strain by the angular strain estimator 112. Also preferably, correlated ultrasound baseband signals obtained from different frames are used to estimate strain without displacement computations. The resulting strain calculation that is derived from the angular strain can be used by clinicians to determine object strain 114, among other things. The object includes tissues, aggregates of cells, internal or external organs, and other bodily or implanted structures.

Figure 2:
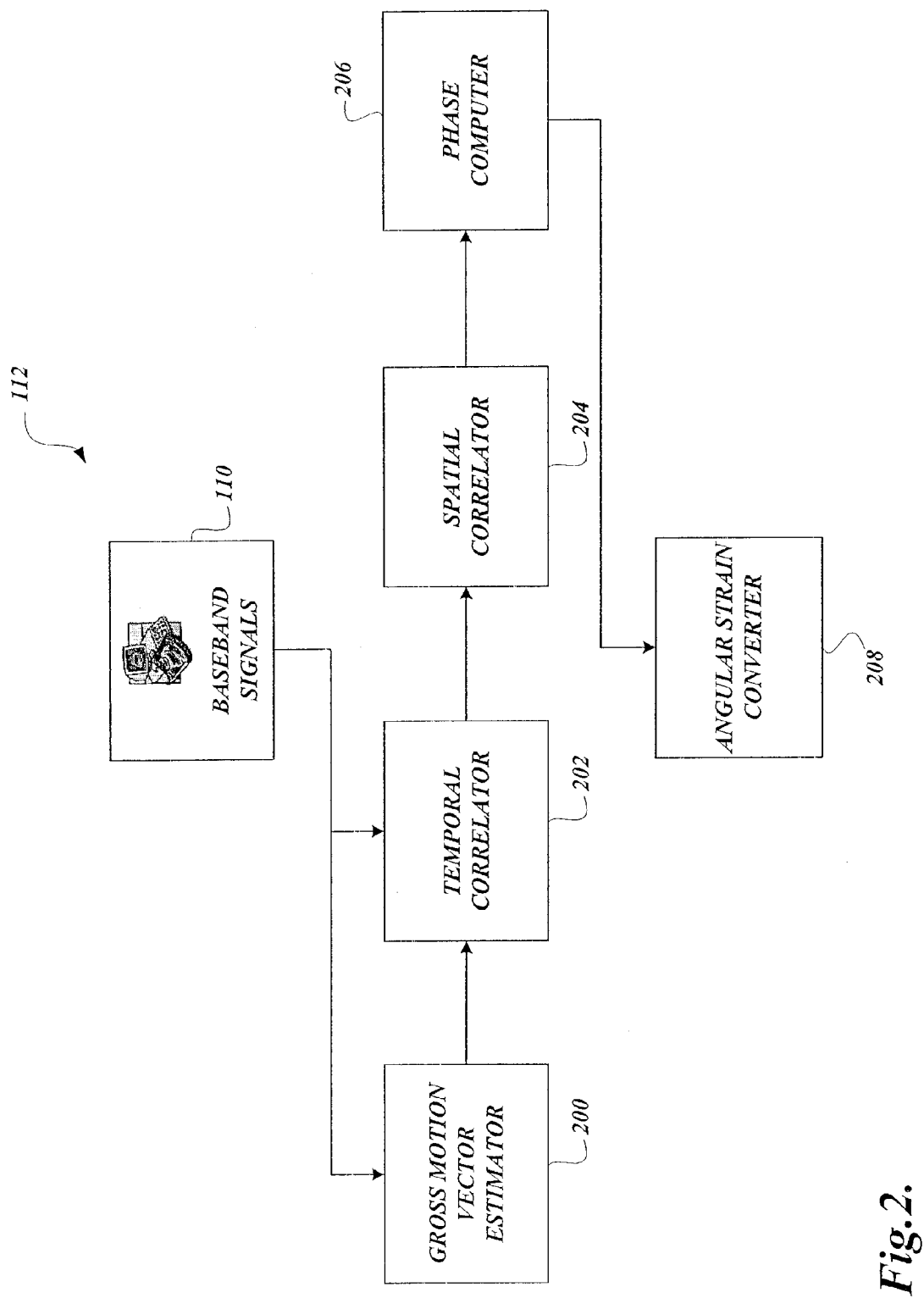
FIG. 2 is a block diagram illustrating an exemplary system for calculating an angular strain, which can be converted directly to strain.

FIG. 2 illustrates the angular strain estimator 112 in more detail. The baseband signals 110 are presented to a gross motion vector estimator 200 and a temporal correlator 202. The gross motion vector estimator 200 estimates gross motion vectors to find locations of correlated signals in pre-compression frames and post-compression frames in the baseband signals 110. A gross motion vector preferably indicates a distance in terms of the number of samples between two correlated signals from different frames. Any suitable motion estimation technique, such as block matching techniques that include cross-correlation or the sum of absolute differences, can be used by the gross motion vector estimator 200 to estimate gross motion vectors. Many other suitable motion estimation techniques can be used, including those that perform a full block matching search (but those that perform a coarse block matching search will suffice as well). As will be appreciated by one skilled in the art, the gross motion vectors roughly indicate where a portion of an object being imaged or the imaged object is located between two frames of the baseband signals and need not be exact.

The temporal correlator 202 receives the gross motion vectors from the gross motion vector estimator 200 and baseband signals 110 to calculate a temporal correlation. The temporal correlator 202 then presents the temporal correlation to a spatial correlator 204, which calculates the spatial correlation. The spatial correlation is then presented to a phase computer 206 which calculates the argument or the phase of a complex number representing the spatial correlation. Alternatively, aliasing could be used to help compute the phase instead of using the spatial correlation. The phase is then presented to an angular strain converter 208, which converts the angular strain to the strain of the object imaged by the ultrasound signals. Alternatively, the angular strain can be directly displayed on a screen or used for further characterization of the imaged object (instead of strain estimation having to be used). Additionally, spatial filters, such as a boxcar filter or median filter, can be applied at any step to estimate strain in various embodiments of the present invention. Moreover, center frequency estimation or frequency variance compensation can be applied for more accurate conversion of angular strain to strain.

Figure 3:
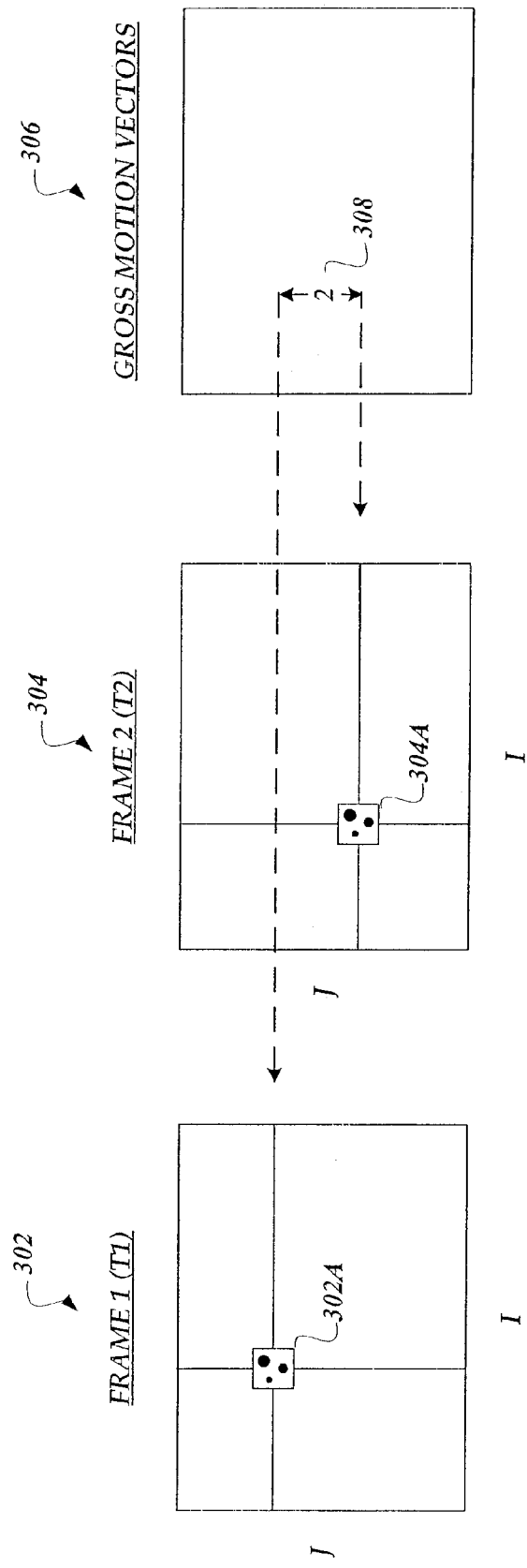
FIG. 3 is a pictorial diagram illustrating the calculation of gross motion vectors involving the use of different frames of baseband signals obtained at different times.
Figure 4A:
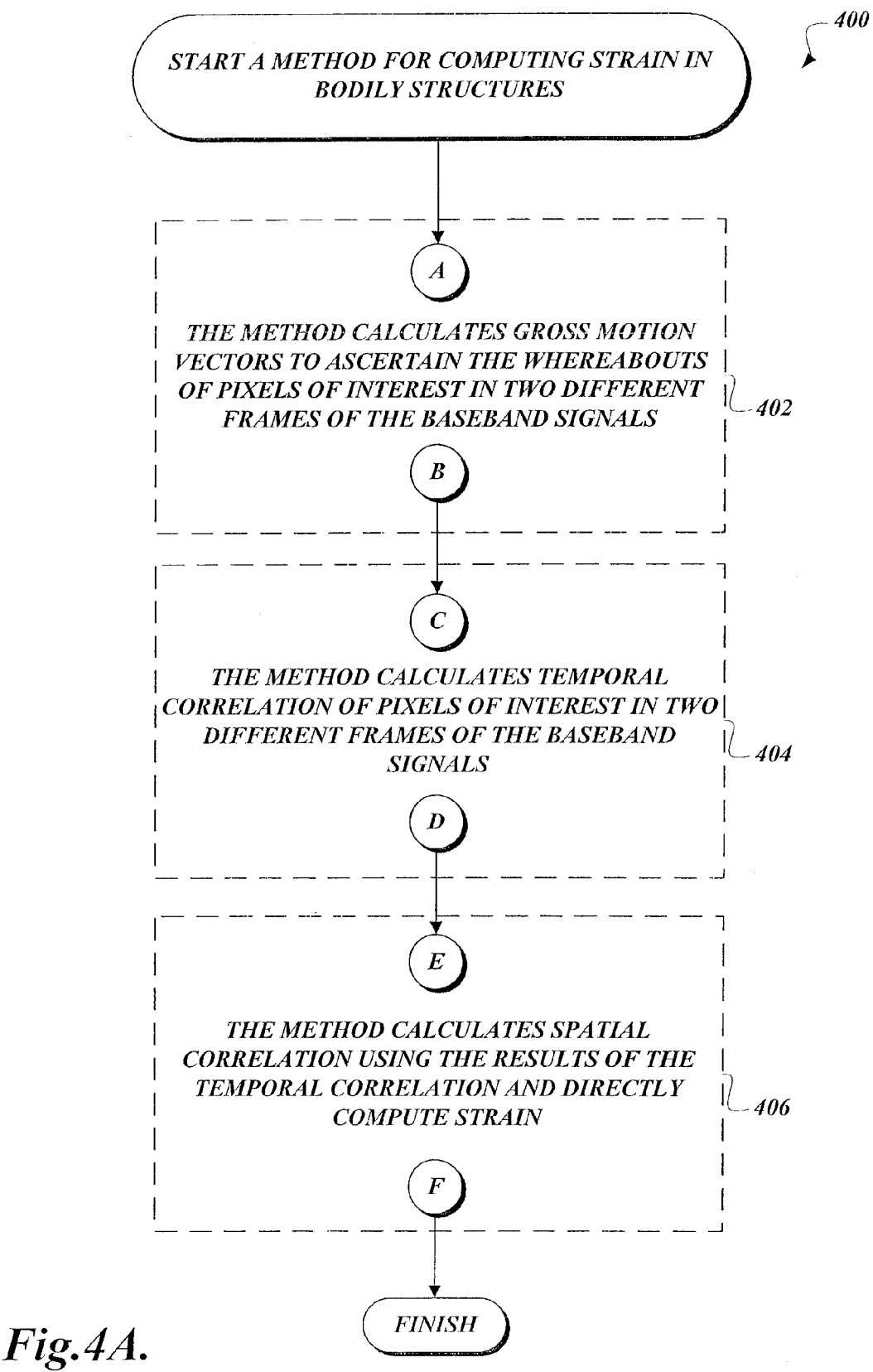
FIGS. 4A-4H are process diagrams illustrating a method for computing strain in bodily structures, including the computation of temporal and spatial correlation.
Figure 4B:
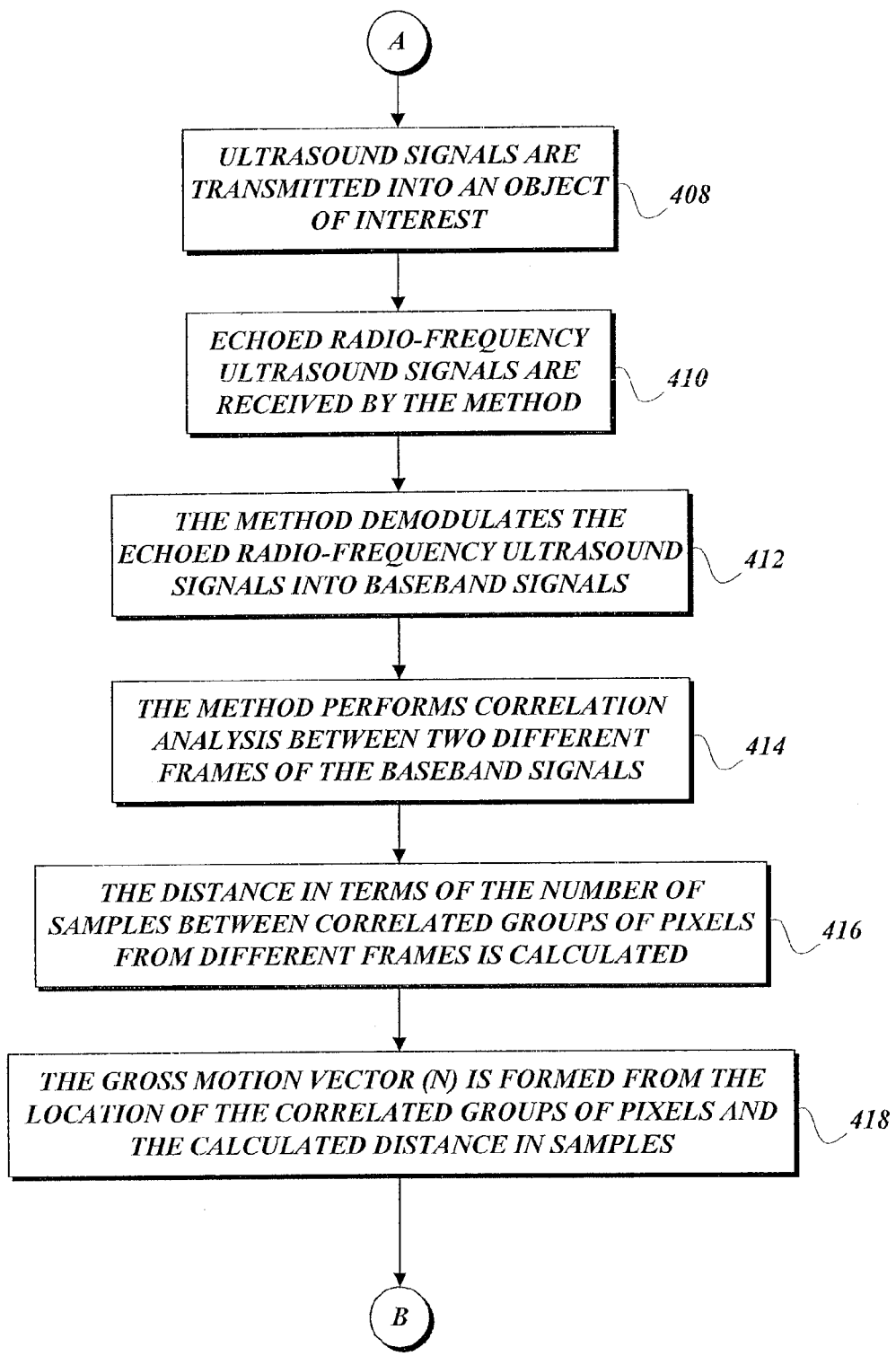
Figure 4C:
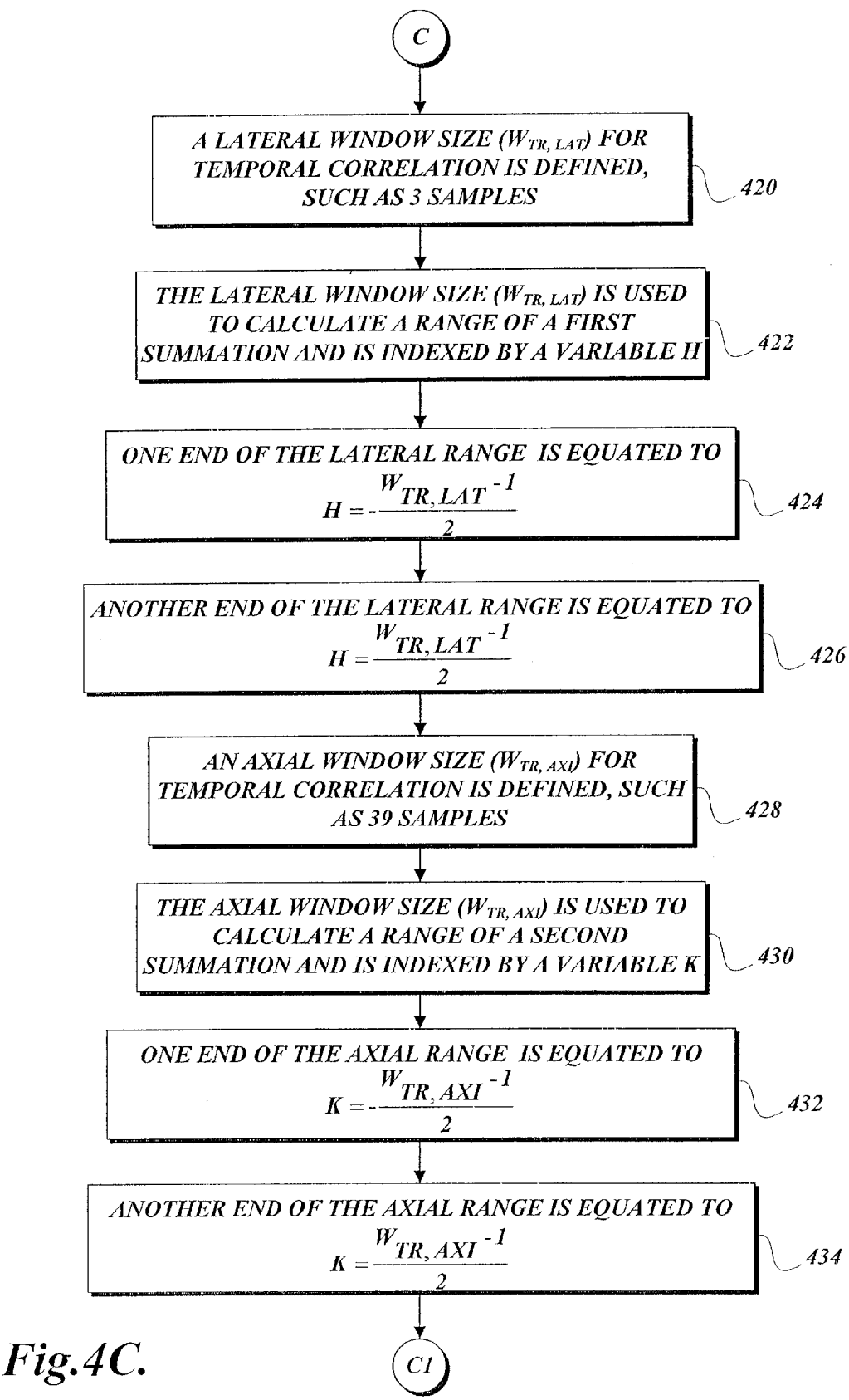
Figure 4D:
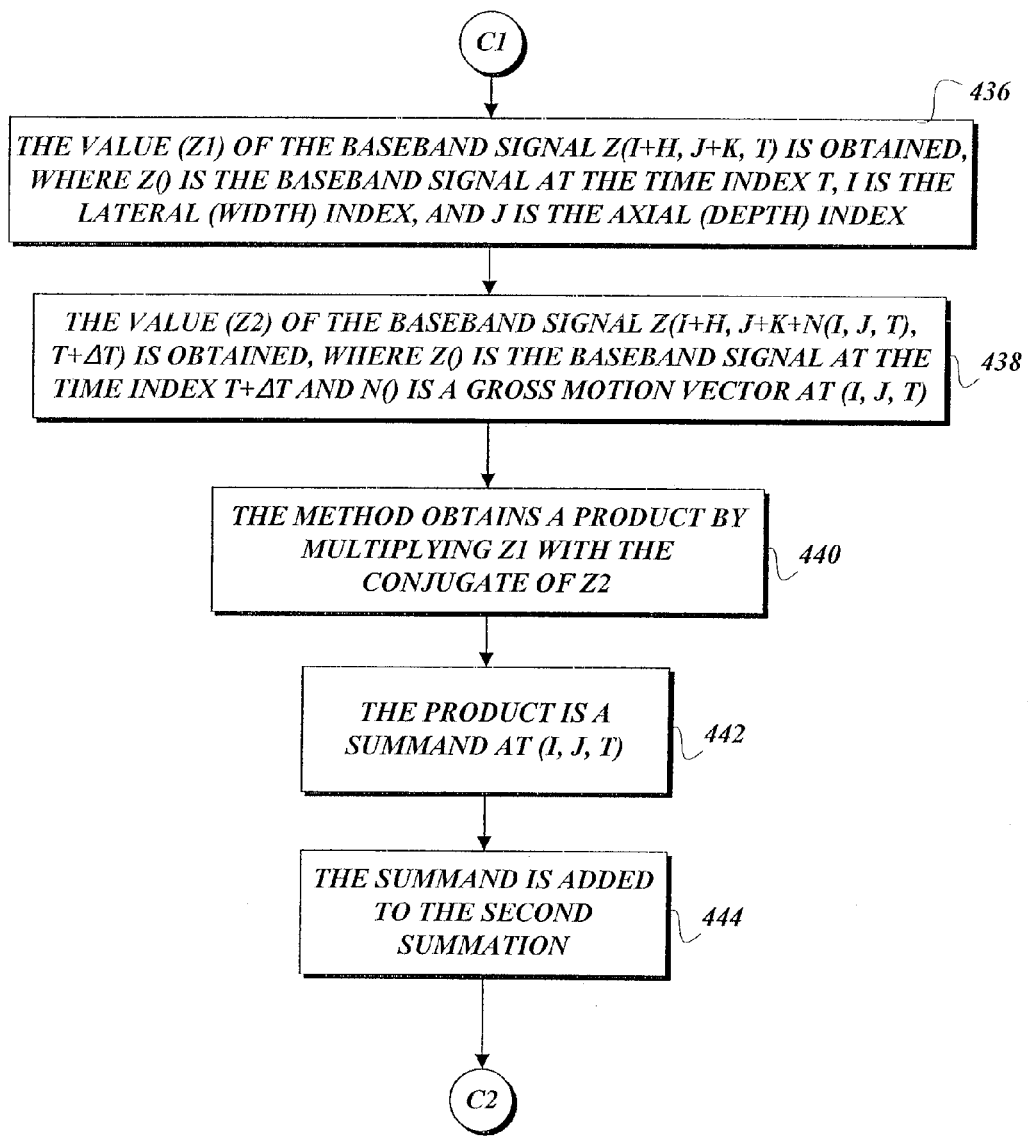
Figure 4E:
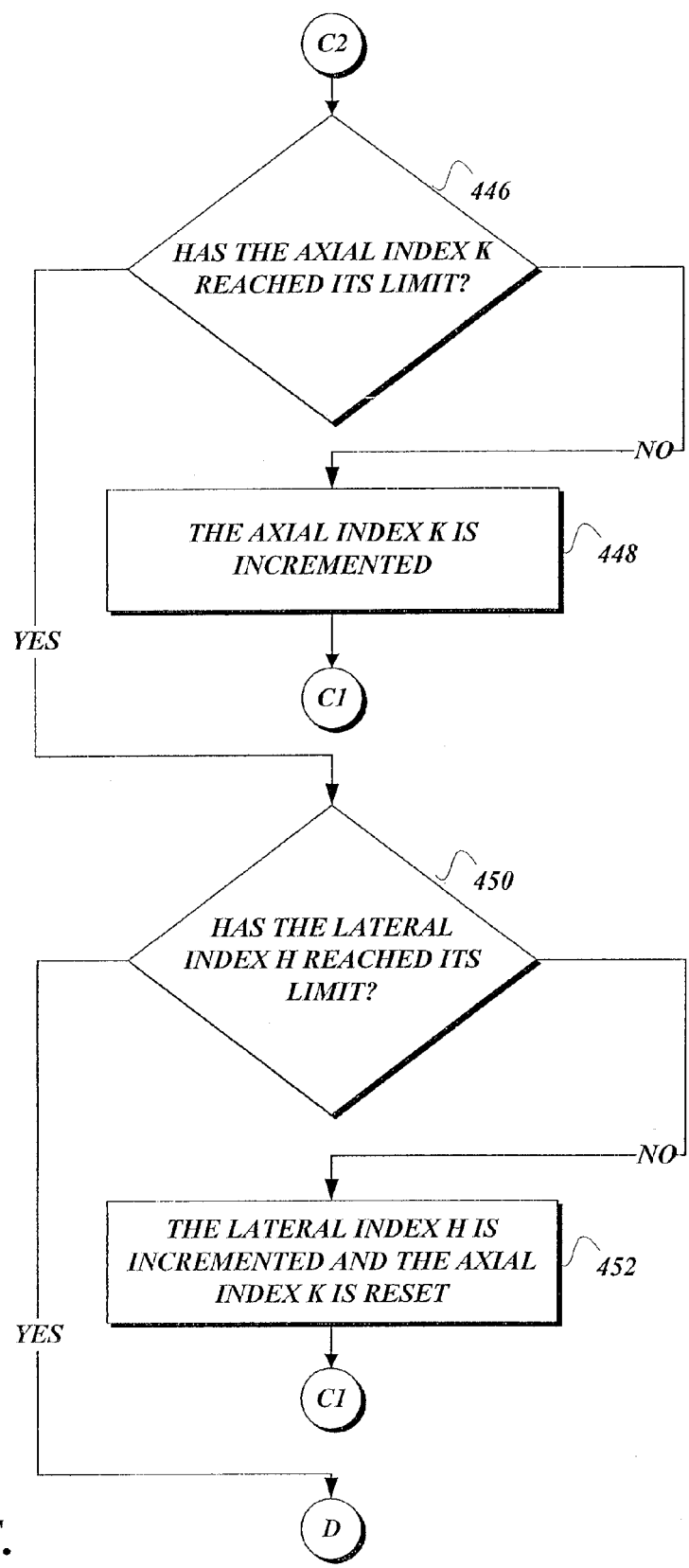
Figure 4F:
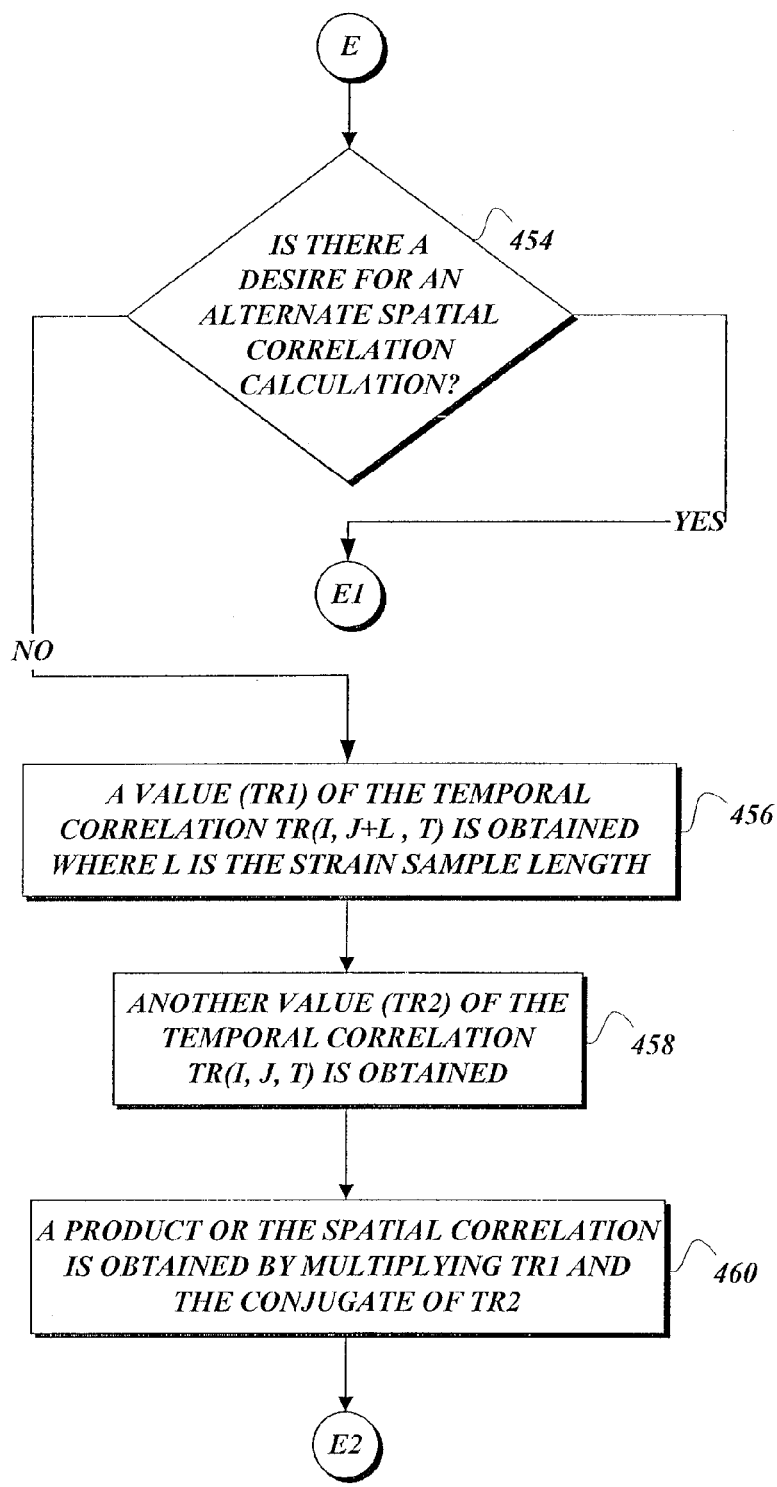
Figure 4G:
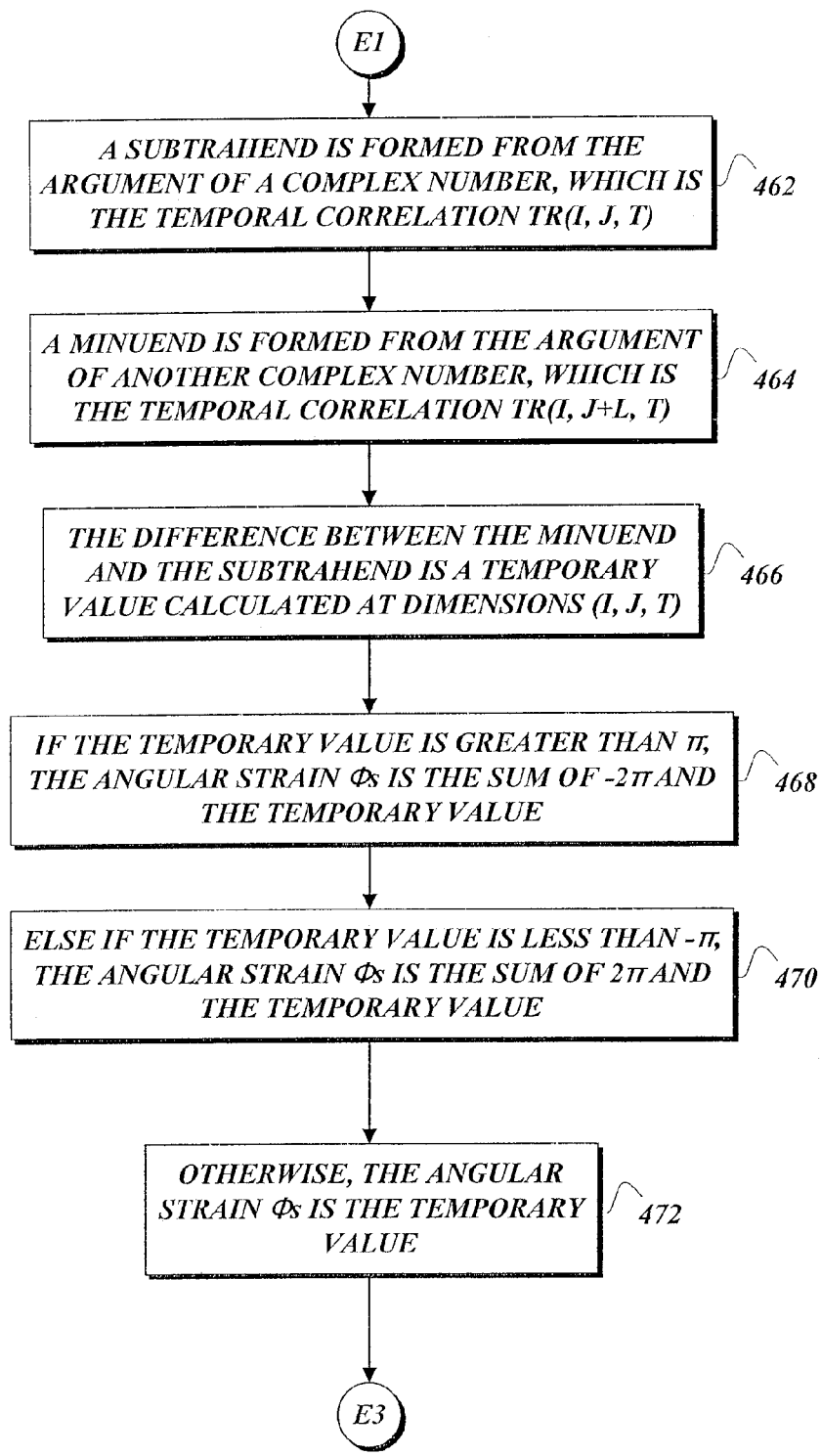
Figure 4H:
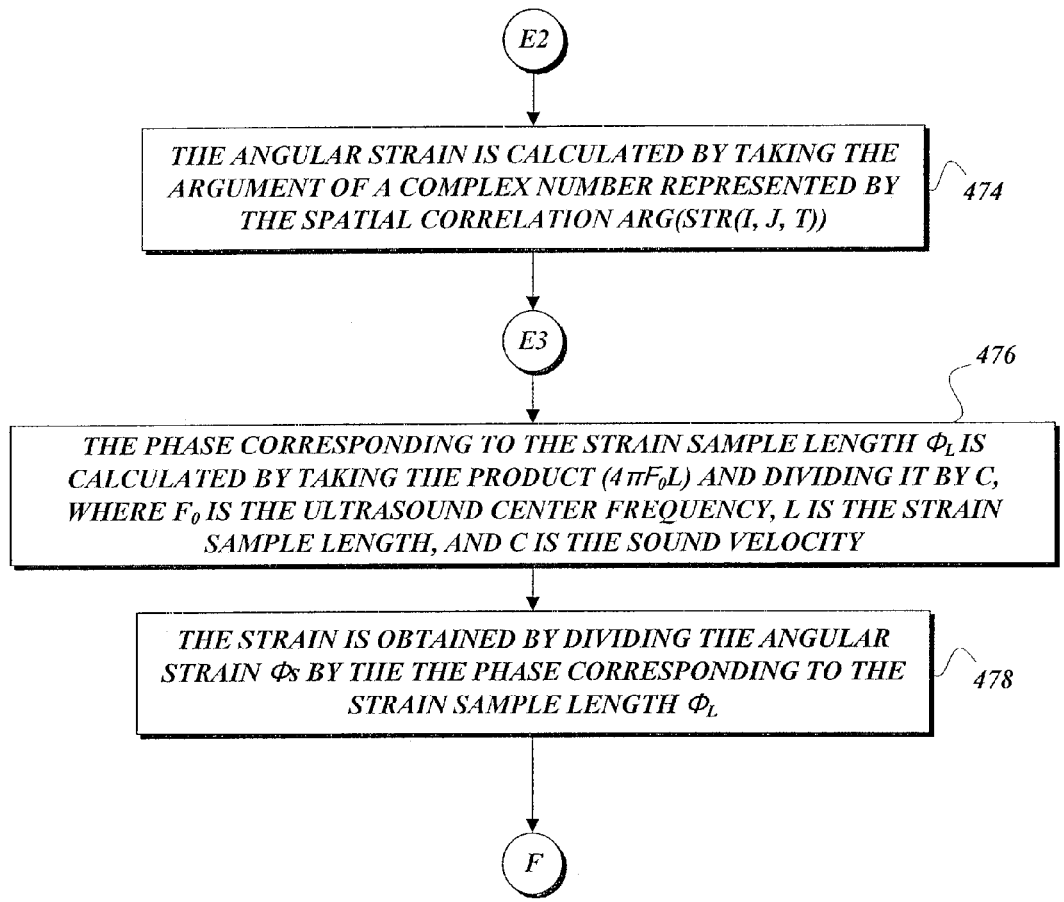

FIG. 3 illustrates pictorially the calculation of a gross motion vector. A frame 302 has a nomenclature "FRAME 1" taken at time T1 of the baseband signals 110. Another frame 304 has the nomenclature "FRAME 2" taken at time T2 of the baseband signals 110. Within the frame 302 is a group 302a of pixels of interest that represent a portion of an object 104 or the object 104 being imaged. The centroid of the group 302a can be identified by indexes I, J, which define the dimensions of the frame 302. The frame 304 occurs at a time different from the time at which the frame 302 occurs. Similar to the frame 302, the frame 304 is indexed by indices I, J, which together define the dimensions of the frame 304. Frames 302, 304 denote distinct periods of time during which ultrasound samples are obtained from the baseband signals 110. Each frame 302, 304 can be displayed by taking its envelope information and rendering the envelope information on a grayscale screen. Each frame is a collection of information formed from complex numbers.

A group 304a consists of pixels of interest that can be determined to be correlated with the group 302a by any suitable motion estimation technique. If the group 302a and the group 304a are correlated, a gross motion vector 308 can be defined to determine the magnitude by which the group 302a in the frame 302 has moved by looking at the location of the group 304a in the frame 304. To provide a concrete example, suppose that the group 302a is located at (2, 3) and the group 304a is located at (2, 1). Because the groups 302a, 304a are correlated, the number 2 indicates the number of samples separating the group 302a and the group 304a. Thus, the gross motion vector for the group 302a at (2, 3) is 2. However, the gross motion vector 308 can be of any suitable magnitude to show the extent to which the group 302a has moved from its original position. In those cases where the object deforms not only axially but also in other directions, a window and a search range may be defined to reflect the movement of the object in other directions. Although FIG. 3 illustrates only axial movement by the group 302a, one with ordinary skill in the art would appreciate that the group 302a consists of pixels of interest that may move not only axially but can also be moved laterally as well.

FIGS. 4A-4H illustrates a method 400 for computing the strain of bodily structures. The method 400 or a portion of it can be implemented by software executing on any programmable computer or by hardware, such as application specific integrated circuits, field programmable gate arrays, field programmable logic devices. From a start block, the method 400 proceeds to a set of method steps 402 defined between a continuation terminal ("Terminal A") and another continuation terminal ("Terminal B"). The set of method steps 402 calculates gross motion vectors to ascertain the whereabouts of pixels of interest in two different frames of the baseband signals 110. Artificial compression or natural compression of objects to be imaged can occur and strain can be calculated. Various embodiments of the present invention are not limited to artificial compression, such as by pressing on an object to be imaged.

From Terminal A (FIG. 4B), the method 400 proceeds to block 408 where ultrasound signals are transmitted into an object of interest. See FIG. 1. Echoed radio-frequency ultrasound signals are received by the method at block 410. Next at block 412, the method demodulates the echoed radio-frequency ultrasound signals into baseband signals. The method 400 then performs correlation analysis between two different frames of the baseband signals by using any suitable motion estimation technique. See block 414. At block 416, the distance in terms of the number of samples between correlated groups of pixels from different frames is calculated. Next at block 418, the gross motion vector (N) is formed from the location of the correlated groups of pixels and the calculated distance in samples. The method 400 then continues to Terminal B.

From Terminal B (FIG. 4A), the method 400 proceeds to another set of method steps 404 defined between a continuation terminal ("Terminal C") and another continuation terminal ("Terminal D"). The set of method steps 404 calculates the temporal correlation of pixels of interest in two different frames of the baseband signals 110.

From Terminal C (FIG. 4C), the method 400 proceeds to block 420 where a lateral window size ($W_{TR,LAT}$) for temporal correlation is defined, such as three samples. Next at block 422, the lateral window size ($W_{TR,LAT}$) is used to calculate a range of a first summation and is indexed by a variable H. One end of the lateral range is equated to $$h = -\frac{W_{TR,LAT} - 1}{2} \quad (3)$$

See block 424. At block 426, another end of the lateral range is equated to $$h = \frac{W_{TR,LAT} - 1}{2}. \quad (4)$$

The method 400 continues to block 428 where an axial window size ($W_{TR,AXI}$) for temporal correlation is defined, such as 39 samples. Preferably, a window size between 0.5-2 mm is used; for a sampling frequency of 30 MHz, a 1 mm window size is approximately 39 samples. At block 430, the axial window size ($W_{TR,AXI}$) is used to calculate a range of a second summation and is indexed by a variable K. One end of the axial range is equated to $$k = -\frac{W_{TR,AXI} - 1}{2} \quad (5)$$

See block 432. Next at block 434 another end of the axial range is equated to $$k = \frac{W_{TR,AXI} - 1}{2} \quad (6)$$

The method 400 then continues at another continuation terminal ("Terminal C1").

From Terminal C1 (FIG. 4D), the method continues to block 436, at which the value (Z1) of the baseband signal Z(I+H,J+K,T) is obtained, where Z( ) is the baseband signal at the time index T, I is the lateral (width) index, and J is the axial (depth) index. At block 438, another value (Z2) of the baseband signal Z(I+H,J+K+N(I,J,T), T+ΔT) is obtained, where Z( ) is the baseband signal at the time index T+ΔT and N( ) is a gross motion vector at (I,J,T). In an embodiment where the gross motion vector is not restricted to the distance of correlated signals in the axial direction only, the gross motion vector can represent three dimensional movement of an object ($N_1,N_2,N_3$), and in which case the value (Z2) of the baseband signal Z(I+H+$N_1$(I,J,T), J+K+$N_2$(I,J,T), T+ΔT) is obtained. The method 400 then proceeds to block 440 where the method obtains a product by multiplying Z1 with a conjugate of Z2. The product is a summand at (I,J,T). See block 442. The summand is added to the second summation. See block 444. The method 400 then continues to another continuation terminal ("Terminal C2").

From Terminal C2 (FIG. 4E), the method 400 proceeds to decision block 446 where a test is performed to determine whether the axial index K has reached its limit. If the answer is NO to the test at decision block 446, the axial index K is incremented. See block 448. The method 400 then proceeds to Terminal C1 where it loops back to block 436 and repeats the above-discussed processing steps. Otherwise, if the answer to the test at decision block 446 is YES, the method 400 continues to another decision block 450 where another test is performed to determine whether the lateral index H has reached its limits. If the answer is NO to the test at decision block 450, the lateral index H is incremented and the axial index K is reset. See block 452. The method then continues to Terminal C1 where it loops back to block 436 and the above-identified processing steps are repeated. Otherwise, if the answer to the test at decision block 450 is YES, the method 400 continues to Terminal D.

From Terminal D (FIG. 4A), the method 400 proceeds to a set of method steps 406 defined between a continuation terminal ("Terminal E") and another continuation terminal ("Terminal F"). The set of method steps 406 calculates spatial correlation using the results of the temporal correlation and directly computes strain.

From Terminal E (FIG. 4F), the method 400 proceeds to decision block 454 where a test is performed to determine whether there is a desire for an alternate spatial correlation calculation. If the answer to the test at decision block 454 is YES, the method 400 continues to another continuation terminal ("Terminal E1"). Otherwise, if the answer to the test at decision block 454 is NO, the method 400 proceeds to block 456 where a value (TR1) of the temporal correlation TR(I,J+L,T) is obtained where L is the strain sample length. Next at block 458, another value (TR2) of the temporal correlation TR(I,J,T) is obtained. At block 460, a product for the spatial correlation is obtained by multiplying TR1 and the conjugate of TR2. The method 400 then continues to another continuation terminal ("Terminal E2").

From Terminal E1 (FIG. 4G), a subtrahend is formed from the argument of a complex number, which is the temporal correlation TR(I,J,T). See block 462. At block 464, a minuend is formed from the argument of another complex number, which is the temporal correlation TR(I,J+L,T). The method 400 then proceeds to block 466 where the difference between the minuend and the subtrahend is a temporary value calculated at dimension (I,J,T). If the temporary value is greater than π, the angular strain $\Phi_S$ is the sum of $-2\pi$ and the temporary value. See block 468. Otherwise, at block 470, if the temporary value is less than $-\pi$, the angular strain $\Phi_S$ is the sum of $2\pi$ and the temporary value. See block 470. Otherwise, at block 472, the angular strain $\Phi_S$ is the temporary value. The method then continues to another continuation terminal ("Terminal E3").

From Terminal E2 (FIG. 414), the method 400 proceeds to block 474 where the angular strain is calculated by taking the argument of a complex number represented by the spatial correlation ARG(STR(I,J,T)). The method 400 continues to Terminal E3 which then continues to block 476 where the phase corresponding to the strain sample length $\Phi_L$ is calculated by taking the product ($4\pi F_0 L$) and dividing it by C, where L is the strain sample length, $F_0$ is the ultrasound carrier frequency, and C is the sound velocity. At block 478, the strain is obtained by dividing the angular strain $\Phi_S$ by the phase corresponding to the strain sample length $\Phi_L$. The method 400 then continues to Terminal F where it terminates execution.

While the preferred embodiment of the invention has been illustrated and described, it will be appreciated that various changes can be made therein without departing from the spirit and scope of the invention.

APPENDIX

As in Eq. (2), strain can be computed by taking a spatial derivative of the displacement. Utilizing the relationship between the displacement and the corresponding phase (angular displacement), $\Phi_d$, strain can be computed as:

$$d(i, j, t) = \frac{c\phi_d(i, j, t)}{4\pi f_0}, \quad (A1)$$

$$\text{strain} = \frac{d(i, j+1, t) - d(i, j, t)}{L}$$

$$= \frac{\phi_d(i, j+1, t) - \phi_d(i, j, t)}{\phi_L}$$

$$= \frac{\phi_s(i, j, t)}{\phi_L}$$

where $\Phi_s$ is the phase corresponding to strain (defined as angular strain) and $\Phi_L$ is the phase corresponding to the strain sample length L. The angular displacement, $\Phi_d$, can be expressed as:

$$\Phi_d(i,j,t) = 2\pi m(i,j,t) + \Phi_m(i,j,t),$$

$$-\pi \leq \Phi_m(i,j,t) < \pi \quad (A2)$$

where m(i,j,t) is an integer value. Then, the change in angular displacements can be derived by:

$$\Phi_d(i,j+1,t) = 2\pi m(i,j+1,t) + \Phi_m(i,j+1,t) \rightarrow \Phi_{d2} = 2\pi m_2 + \Phi_{m2},$$

$$\Phi_d(i,j,t) = 2\pi m(i,j,t) + \Phi_m(i,j,t) \rightarrow \Phi_{d1} = 2\pi m_1 + \Phi_{m1},$$

$$\Phi_{d2} - \Phi_{d1} = 2\pi m_2 + \Phi_{m2} - 2\pi m_1 - \Phi_{m1} = 2\pi(m_2 - m_1) + \Phi_{m2} - \Phi_{m1} \quad (A3)$$

Since the range of $\Phi_{m2} - \Phi_{m1}$ is from $-2\pi$ to $2\pi$, $\Phi_{m2} - \Phi_{m1}$ can be expressed as:

$$\Phi_{m2} - \Phi_{m1} = 2\pi k + \Phi_k,$$

$$k = 0, \pm 1,$$

$$-\pi \leq \Phi_k < \pi \quad (A4)$$

From Eqs. (A1), (A3), and (A4), the angular strain, $\Phi_s$, is $$\Phi_s = \Phi_{d2} - \Phi_{d1} = 2\pi(m_2 - m_1 + k) + \Phi_k,$$

$$k = 0, \pm 1,$$

$$-\pi \leq \Phi_k < \pi \quad (A5)$$

Due to the decorrelation noise for large compression levels, ultrasonic strain estimation is typically limited to small compression levels, such as up to 3%. The angular strain corresponding to the typical compression range in ultrasound elasticity imaging, such as up to 3%, is small enough to be limited within the range of $[-\pi,\pi]$. For example, with the strain sample length (L) of 200 μm and the ultrasound center frequency ($f_0$) of 7.5 MHz, the angular strain corresponding to up to 25% strain does not exceed the range of $[-\pi,\pi]$. This implies that the angular strain to be estimated, $\Phi_s$, is same as $\Phi_k$:

$$-\pi < \Phi_s = \Phi_{d1} = 2\pi(m_2 - m_1 + k) + \Phi_k < \pi,$$

$$\Rightarrow 2\pi(m_2 - m_1 + k) = 0$$

$$\Rightarrow \Phi_s = \Phi_k \quad (A6)$$

$\Phi_k$ can be computed from $\Phi_{m1}$ and $\Phi_{m2}$ based on their relationship defined in Eq. (A4). If a phase-aliasing operator, alias[ ], is defined as:

$$\Phi = 2\pi h + \Phi_h, -\pi < \Phi_h < \pi,$$

$$\text{alias}[\Phi] = \Phi_h \quad (A7)$$

then $\Phi_k$ is the result of the phase aliasing operation using $\Phi_{m1}$ and $\Phi_{m2}$ as:

$$\Phi_k = \text{alias}[\Phi_{m2} - \Phi_{m1}] \quad (A8)$$

In medical ultrasound systems, $\Phi_m$ can be obtained from the phase of the temporal correlation function using correlated baseband signals (TR(i,j,t) in Eq. (A10)) as:

$$\Phi_m(i,j,t) = \arg(TR(i,j,t)) \quad (A9)$$

Where TR(i,j,t) is $$TR(i, j, t) = \sum_{h=-\frac{W_{TR,LAT}-1}{2}}^{\frac{W_{TR,LAT}-1}{2}} \sum_{k=-\frac{W_{TR,AXI}-1}{2}}^{\frac{W_{TR,AXI}-1}{2}} z(i+h, j+k, t) \times \quad (A10)$$

$$z^*(i+h, j+k+n(i, j, t), t+\Delta t)$$

From Eqs. (A8), and (A9), the phase of the temporal and spatial correlation function (STR(i,j,t) in Eq. (A12)) is equivalent to $\Phi_k$ as:

$$\arg(STR(i, j, t)) = \arg(TR(i, j+1, t) \times TR^*(i, j, t)) \quad (A11)$$

-continued $$= \text{alias}[\arg(TR(i, j+1, t)) - \arg(TR(i, j, t))]$$
$$= \text{alias}[\phi_m(i, j+1, t) - \phi_m(i, j, t)]$$
$$= \phi_k(i, j, t)$$

Where STR(i,j,t) is $$STR(i,j,t) = TR(i,j+L,t) \times TR^*(i,j,t) \qquad (A12)$$

From Eqs. (A6) and (A11), the angular strain, $\Phi_s$, is same as the phase of the temporal and spatial correlation function as:

$$\Phi_s(i,j,t) = \Phi_k(i,j,t) = \arg(STR(i,j,t)) \qquad (A13)$$

The embodiments of the invention in which an exclusive property or privilege is claimed are defined as follows:

1. A computer-implemented method for calculating strain, comprising:
   transmitting and acquiring ultrasound signals echoed from an object before the object is compressed and after the object is compressed; and
   estimating an amount of deformation of the object by using the phase of temporal and spatial correlation between ultrasound baseband signals from different frames so as to determine strain without estimating displacement, the estimated deformation being based on an argument of a complex number representing the spatial or temporal correlation.

2. The method of claim 1, wherein the act of transmitting and acquiring includes acquiring baseband signals by demodulating the echoed ultrasound signals.

3. The method of claim 2, further comprising estimating gross motion vectors to identify locations of correlated signals in frames that are acquired prior to the object being compressed and in frames that are acquired after the object is compressed.

4. The method of claim 3, further comprising estimating an angular strain, which corresponds to the amount of deformation, the angular strain being a quotient with a dividend being a product of 4, π, the carrier frequency of the ultrasound signals, and the amount of deformation in the object under force, and a divisor being the sound velocity.

5. The method of claim 4, wherein the act of estimating the amount of deformation of the object includes converting the angular strain to the strain by finding a quotient with the angular strain as a dividend and a normalization term as a divisor, the normalization term being a quotient where a dividend is a product of 4, π, the carrier frequency of the ultrasound signals, and the length of the object, and a divisor being the sound velocity.

6. The method of claim 4, wherein the act of estimating the angular strain includes computing a temporal correlation which is a function of three variables (i,j,t), the variable i being the width index, the variable j being the depth index, and the variable t being the time index, the function of the temporal correlation being equated to a summation of summands, each summand being a product from a first quantity and a conjugate of a second quantity, the first quantity being a function of three variables that describes the baseband signal at (i+h,j+k,t), and the second quantity being a function of three variables that describes the baseband signal at (i+h, j+k+n(i,j,t), t+Δt).

7. The method of claim 6, wherein each summand of the summation is indexed with a lateral index h and an axial index k, both the lateral index h and the axial index k being equated to a quotient whose dividend is a window size calculated in the number of samples minus 1 and whose divisor is 2, the indices h and k ranging from a negative quotient to a positive quotient.

8. The method of claim 7, wherein a function n(i,j,t) describes a gross motion vector.

9. The method of claim 8, further comprising calculating spatial correlation which is a function of variables (i,j,t) and the strain sample length L, the function of the spatial correlation being equated to a correlation that is a product of a first quantity and a conjugation of a second quantity, the first quantity being the temporal correlation whose inputs include (i,j+L,t), and the second quantity being the temporal correlation whose inputs include (i,j,t).

10. The method of claim 9, wherein the act of estimating the angular strain estimates the angular strain at (i,j,t) by deriving the phase of the spatial correlation, the phase being the argument of a complex number defined by the spatial correlation at (i,j,t).

11. A non-transitory computer-readable medium having computer-executable instructions thereon for implementing a method for calculating strain, comprising:
    transmitting and acquiring ultrasound signals echoed from an object before the object is compressed and after the object is compressed; and
    estimating an amount of deformation of the object by using the phase of temporal and spatial correlation between ultrasound baseband signals from different frames so as to determine strain without estimating displacement, the estimated deformation being based on an argument of a complex number representing the spatial or temporal correlation.

12. The non-transitory computer-readable medium of claim 11, further comprising estimating gross motion vectors to identify locations of correlated signals in frames that are acquired prior to the object being compressed and in frames that are acquired after the object is compressed.

13. The non-transitory computer-readable medium of claim 12, further comprising estimating an angular strain, which corresponds to the amount of deformation, the angular strain being a quotient with a dividend being a product of 4, π, the carrier frequency of the ultrasound signals, and the amount of deformation of the object under uni-axial force, and a divisor being the sound velocity.

14. The non-transitory computer-readable medium of claim 13, wherein the act of estimating the amount of deformation of the object includes converting the angular strain to the strain by finding a quotient with the angular strain as a dividend and a normalization term as a divisor, the normalization term being a quotient where a dividend is a product of 4, π, the carrier frequency of the ultrasound signals, and the length of the object, and a divisor being the sound velocity.

15. The non-transitory computer-readable medium of claim 13, wherein the act of estimating the angular strain includes computing a temporal correlation which is a function of three variables (i,j,t), the variable i being the width index, the variable j being the depth index, and the variable t being the time index, the function of the temporal correlation being equated to a summation of summands, each summand being a product from a first quantity and a conjugate of a second quantity, the first quantity being a function of three variables that describes the baseband signal at (i+h,j+k,t), and the second quantity being a function of three variables that describes the baseband signal at (i+h,j+k+n(i,j,t), t+Δt).

16. The non-transitory computer-readable medium of claim 15, further comprising calculating spatial correlation which is a function of variables (i,j,t) and the strain sample length L, the function of the spatial correlation being equated to a correlation that is a product of a first quantity and a conjugation of a second quantity, the first quantity being the temporal correlation whose inputs include (i,j+L,t), and the second quantity being the temporal correlation whose inputs include (i,j,t).

17. The non-transitory computer-readable medium of claim 16, wherein the act of estimating the angular strain estimates the angular strain at (i,j,t) by deriving the phase of the spatial correlation, the phase being the argument of a complex number defined by the spatial correlation at (i,j,t).

18. A computer-implemented method for calculating strain, comprising:
   transmitting and acquiring ultrasound signals echoed from an object before the object is compressed and after the object is compressed; and
   estimating an amount of deformation of the object by using the phase of temporal and spatial correlation between ultrasound baseband signals from different frames so as to determine strain without estimating displacement,
   wherein determining the strain without estimating displacement further includes estimating an angular strain which corresponds to the amount of deformation, the angular strain being calculated by taking an argument of a complex number representing the spatial correlation, the angular strain being a quotient with a dividend being a product of 4, $\pi$, the carrier frequency of the ultrasound signals, and the amount of deformation in the object under force, and a divisor being the sound velocity.

* * * * *